US008822729B2

(12) United States Patent
Gaspar et al.

(10) Patent No.: US 8,822,729 B2
(45) Date of Patent: Sep. 2, 2014

(54) METHOD FOR PROVIDING A SECONDARY OR TERTIARY AMINE

(71) Applicants: Huntsman International LLC, The Woodlands, TX (US); Huntsman Corporation Hungary ZRt, Petfurdo (HU)

(72) Inventors: Zsolt Gaspar, Petfurdo (HU); Heiko H. Humbert, Hamburg (DE); Gabor Felber, Veszprem (HU); Attila Gaspar, Petfurdo (HU); Robert A Grigsby, Jr., Spring, TX (US); Imre Kordas, Veszprem (HU); Petra Emma Vanderstraeten, Leuven (BE)

(73) Assignees: Huntsman International LLC, The Woodlands, TX (US); Huntsman Corporation Hungary Zrt, Petfurdo (HU)

( * ) Notice: Subject to any disclaimer, the term of this patent is extended or adjusted under 35 U.S.C. 154(b) by 0 days.

(21) Appl. No.: 14/104,599

(22) Filed: Dec. 12, 2013

(65) Prior Publication Data

US 2014/0155655 A1 Jun. 5, 2014

Related U.S. Application Data

(62) Division of application No. 13/375,497, filed as application No. PCT/EP2010/056144 on May 6, 2010, now Pat. No. 8,664,445.

(60) Provisional application No. 61/183,168, filed on Jun. 2, 2009.

(30) Foreign Application Priority Data

Jun. 29, 2009 (EP) .................................. 09462005

(51) Int. Cl.
*C07C 217/42* (2006.01)
*C09K 3/00* (2006.01)
*C07C 217/08* (2006.01)
*C08G 18/48* (2006.01)
*C07C 213/02* (2006.01)
*C08G 18/28* (2006.01)
*C08G 18/18* (2006.01)
*C08G 101/00* (2006.01)

(52) U.S. Cl.
CPC ............. *C07C 217/42* (2013.01); *C07C 217/08* (2013.01); *C08G 18/4812* (2013.01); *C07C 213/02* (2013.01); *C08G 2101/0025* (2013.01); *C08G 18/2825* (2013.01); *C08G 18/1833* (2013.01)
USPC ....... 564/504; 564/512; 252/182.23

(58) Field of Classification Search
CPC ...................................................... C07C 217/42
USPC ................................................... 564/504, 512
See application file for complete search history.

(56) References Cited

U.S. PATENT DOCUMENTS

| 4,408,075 | A | 10/1983 | Soula et al. |
| 5,344,984 | A | 9/1994 | Knifton et al. |
| 6,403,834 | B1 | 6/2002 | Alas et al. |

FOREIGN PATENT DOCUMENTS

| DE | 848 825 | 9/1952 |
| DE | 26 18 280 | 11/1977 |
| EP | 0 214 852 | 3/1987 |
| EP | 0 839 575 | 5/1998 |

OTHER PUBLICATIONS

Database Caplus in STN, Acc. No. 1962:41779, Lewis et al., Journal of Pharmacy and Pharmacology (1961), 13, p. 543-547 (abstract).*
International Search Report and Written Opinion regarding corresponding application No. PCT/EP2010/056144, dated Jun. 28, 2010.
Whitmore, F. C., et al., "Basically Substituted Aliphatic Nitriles and their Catalytic Reduction to Amines", J. Am. Chem. Soc., vol. 66, No. 5 (1944), p. 725-731.
Bachman, G. B., et al., "Preparation of Various Complex Aliphatic Amines", J. Org. Chem., vol. 10, No. 3 (1945), p. 243-254.
Protiva, M., et al. "Synthetische Analoga der Kurare-Alkaloide I. Quartare, von Polybasischen Aliphatischen Athern and Thioathern Abgeleitete Salze" Collection Czechoslov. Chem. Commun., vol. 18 (1953) p. 836-840.
Edwards, D., et al. "Neuromuscular blocking agents", J. Pharmacy and Pharmacology, vol. 12 (1960), p. 137T-152T.
Lewis, J. J., et al. "Neuromuscular blocking agents", J. Pharmacy and Pharmacology, vol. 13 (1961) p. 543-547.

* cited by examiner

*Primary Examiner* — Brian J Davis
(74) *Attorney, Agent, or Firm* — Monique M. Raub

(57) ABSTRACT

A method for providing a secondary or tertiary amine with formula $(R^1R^2NR^3)_2NR^4$ is provided, wherein
each of $R^1$ and $R^2$ are chosen from the group consisting of a methyl group, an ethyl group, an iso-propyl group and an n-propyl group;
$R^3$ being an alkoxyalkyl group chosen from the group consisting of —CH2CH2OCH2CH2—, —CH2CH2OCH2CH2— and —CH2CH2CH2OCH2CH2CH2—;
$R^4$ is chosen from the group consisting of a hydrogen, a methyl group, an ethyl group, an iso-propyl group, an n-propyl group and a group with formula $R^1R^2NR^3$.
The method comprises the steps:
(α) reacting $R^1R^2NR^3(OH)$ with ammonia, thereby providing a mixture comprising $(R^1R^2NR^3)_2NR^4$;
(β) separating $(R^1R^2NR^3)_2NR^4$ from said mixture.

4 Claims, No Drawings

METHOD FOR PROVIDING A SECONDARY OR TERTIARY AMINE

CROSS-REFERENCE TO RELATED APPLICATIONS

This application is a divisional of U.S. patent application Ser. No. 13/375,497, pending, which is the National Phase of International Application PCT/EP2010/056144 filed May 6, 2010 which designated the U.S. and which claims priority to EP Application No. 09462005.1 filed Jun. 29, 2009 and U.S. Provisional Application No. 61/183,168 filed Jun. 2, 2009. The noted applications are incorporated herein by reference.

The invention relates to the provision of secondary and/or tertiary amines with formula $(R^1R^2NR^3)_2NR^4$ wherein each of $R^1$ and $R^2$ are chosen from the group consisting of a methyl group, an ethyl group, an iso-propyl group and an n-propyl group;

$R^3$ being an alkoxyalkyl group chosen from the group consisting of $-CH_2CH_2OCH_2CH_2-$, $-CH_2CH_2OCH_2CH_2CH_2-$ and $-CH_2CH_2CH_2OCH_2CH_2CH_2-$;

$R^4$ is chosen from the group consisting of a hydrogen, a methyl group, an ethyl group, an iso-propyl group, an n-propyl group and a group with formula $R^1R^2NR^3$, and to methods to do so.

The present invention relates to methods for providing, separating and/or recovering such amines, in particular to amines of the type bis(N,N-2-dialkylaminoalkoxyalkyl)amine as well as the provision of alkylated bis(N,N-2-dialkylaminoalkoxyalkyl)amine.

In particular the invention relates to the provision of bis-(N,N-2-dimethylaminoethoxyethyl)amine and/or bis-(N,N-2-dimethylaminoethoxyethyl)methylamine.

$(R^1R^2NR^3)_2NR^4$ wherein each of $R^1$ and $R^2$ are a methyl group, $R^3$ being $-CH_2CH_2OCH_2CH_2-$ and $R^4$ being a methyl group, also named bis-(N,N-2-dimethylaminoethoxyethyl)methylamine, is known as a chemical compound, used as polyurethane catalysts or as precursors for the provision of polyurethane catalysts, as is set out in DE2618280. Bis-(N,N-2-dimethylaminoethoxyethyl)methylamine, made according to DE2618280, i.e. made from chlorinated sulphur and/or phosphorous compounds, is known to keep traces of those elements, even in the "purified" end-product. Further, some of the base products used in the process of DE2618280 are extremely toxic, hazardous and dangerous to store, handle or transport. They are not suitable to be used on economically viable scale in a chemical process. The compound bis-(N,N-2-dimethylaminoethoxyethyl)amine, or $(R^1R^2NR^3)_2NR^4$ wherein each of $R^1$ and $R^2$ are a methyl group, $R^3$ being $-CH_2CH_2OCH_2CH_2-$ and $R^4$ being hydrogen, is a chemical product which can only be obtained in lab-scale quantities.

For both products, there is a need for a production method, providing the compound on economically acceptable quantities at acceptable costs. There is also a need for a production method, providing the compounds on economically acceptable quantities, the compounds being substantially pure, and in particular substantially free of chlorine, phosphor and/or sulphur in free or bound form.

The above objective is accomplished by a method according to the present invention.

In a first aspect of the present invention, a method for providing for providing a secondary or tertiary amine with formula $(R^1R^2NR^3)_2NR^4$ is provided, wherein each of $R^1$ and $R^2$ are chosen from the group consisting of a methyl group, an ethyl group, an iso-propyl group and an n-propyl group;

$R^3$ being an alkoxyalkyl group chosen from the group consisting of $-CH_2CH_2OCH_2CH_2-$, $-CH_2CH_2OCH_2CH_2CH_2-$ and $-CH_2CH_2CH_2OCH_2CH_2CH_2-$;

$R^4$ is chosen from the group consisting of a hydrogen, a methyl group, an ethyl group, an iso-propyl group, an n-propyl group and a group with formula $R^1R^2NR^3$, the method comprises the steps:

(α) reacting $R^1R^2NR^3(OH)$ with ammonia, thereby providing a mixture comprising $(R^1R^2NR^3)_2NR^4$;

(β) separating $(R^1R^2NR^3)_2NR^4$ from said mixture.

The molar ratio ammonia/$R^1R^2NR^3(OH)$ may range from 0.5 to 20, preferably ranging from 1 to 6. In particular, when $R^1$ and $R^2$ are methyl and $R^3$ is $-CH_2CH_2OCH_2CH_2-$, the molar ratio ammonia/N,N-2-dimethyl-aminoethoxyethanol may range from 0.5 to 20, preferably ranging from 1 to 6.

It was found that the reaction of ammonia with the $R^1R^2NR^3(OH)$, preferably in presence of a catalyst, provides mixtures of components, which mixtures comprise, next to the corresponding $(R^1R^2NR^3)_2NH$, at least one of a corresponding primary amine $R^1R^2NR^3NH_2$, a secondary amine $R^1R^2NR^3NR^5H$, and/or a tertiary amine $R^1R^2NR^3NR^5R^6$, wherein $R^5$ and optionally $R^6$ are identical to $R^1$ or $R^2$. Further, it was noticed that also other amines, with general formula $(R^1R^2NR^3)_2NR^4$ may be obtained, for which $R^4$ equals either $R^1$, $R^2$ or $(R^1R^2NR^3)$.

Without wishing to be bound by any theory, it is believed that these latter amines are provided by trans-alkylation of the alkyl groups on the amines.

As an example, in case of an alkanol with formula $R^1R^2NR^3(OH)$ wherein each of $R^1$ and $R^2$ are a methyl group, and wherein $R^3$ being an alkoxyalkyl group chosen from the group consisting of $-CH_2CH_2OCH_2CH_2-$, $-CH_2CH_2OCH_2CH_2CH_2-$ and $-CH_2CH_2CH_2OCH_2CH_2CH_2-$, a mixture comprising an amine with formula $((CH_3)_2NR^3)_2NH$, and further comprising a primary amine of the general formula $(CH_3)_2NR^3NH_2$, a secondary amine of formula $(CH_3)_2NR^3NH(CH_3)$ and a tertiary amine with formula $(CH_3)_2NR^3N(CH_3)_2$ may be obtained. Also present in this mixture are components with formula $((CH_3)_2NR^3)_3N$, next to $((CH_3)_2NR^3)_2NCH_3$.

According to some embodiments of the present invention, the $R^1R^2NR^3(OH)$ may be reacted with ammonia in presence of a catalyst.

So-called copper-chromite catalysts are examples of typical oxidic catalysts of Group I B/VI B of Periodic Table of elements, which catalysts are suitable for the reaction of N,N-2-dialkylaminoalkoxyalkanol with ammonia.

Numerous promoters may be used, mainly comprising elements of the Groups I A and II A, IV B, IV A, VIII B. Other suitable catalysts for alcohol amination reaction are supported or non-supported catalysts of the Group of VI B. Carriers for group VIII B metals are $Al_2O_3$, $SiO_2$, $TiO_2$, activated carbon, etc. Also, it is popular to add different promoters to such catalyst, mainly of the Groups I A and II A, IV B, IV A.

Carriers like $Al_2O_3$, $SiO_2$, $TiO_2$ may show appreciable activity for alcohol amination reactions. Promoters can be added, which are covering a wide range of components.

A catalyst load, expressed as LHSV (=liter/liter*h$^{-1}$) based upon the N,N-dimethylaminoethoxyethanol feed, of 0.01 to 2.0, preferably 0.1 to 1 is used.

According to some embodiments of the present invention, $R^1$ may be identical to $R^2$.

According to some embodiments of the present invention, $R^1$ and/or $R^2$ may be methyl.

According to some embodiments of the present invention, $R^3$ may be —CH$_2$CH$_2$OCH$_2$CH$_2$—.

According to some embodiments of the present invention, $R^4$ may be hydrogen.

As such, according to some embodiments of the present invention, an amine with formula $(R^1R^2NR^3)_2NR^4$ may be the secondary amine bis-(N,N-2-dimethyl-aminoethoxy-ethyl)amine.

It was found that the reaction of ammonia with the $R^1R^2NR^3(OH)$, preferably in presence of a catalyst, provides mixtures of components, which mixtures comprise, next to the corresponding $(R^1R^2NR^3)_2NH$, at least one of a corresponding primary amine $R^1R^2NR^3NH_2$, a secondary amine $R^1R^2NR^3NR^5H$, and/or a tertiary amine $R^1R^2NR^3NR^5R^6$, wherein $R^5$ and optionally $R^6$ are identical to $R^1$ or $R^2$.

According to some embodiments of the present invention, the separating of $(R^1R^2NR^3)_2NH$ from the mixture may be done by distillation of said mixture.

The distillation provides different fractions, of which typically the heavy fraction comprises $(R^1R^2NR^3)_2NH$, together with isomers of this molecule. Typically, in case of an amine with formula $(R^1R^2NR^3)_2NH$ wherein each of $R^1$ and $R^2$ are chosen from the group consisting of a methyl group, an ethyl group, an iso-propyl group or an n-propyl group;

$R^3$ being an alkoxyalkyl group chosen from the group consisting of —CH2CH2OCH2CH2—, —CH$_2$CH$_2$OCH$_2$CH$_2$CH$_2$— and —CH$_2$CH$_2$CH$_2$OCH$_2$CH$_2$CH$_2$—.

The heavy fraction comprises $(R^1R^2NR^3)_2NH$, together with corresponding transalkylated amines.

Further other components were found present in the mixture, which further components seem to be various compounds structurally similar to $(R^1R^2NR^3)_2NH$. Such compounds are present up to 20 w %, but typically only up to 15 w % or less. The purity of the $(R^1R^2NR^3)_2NH$, such as bis(N, N-2-dimethylaminoethoxyethyl)amine may range up to 80 w %, even up to 85 w % or more.

In case of bis-(N,N-2-dimethylamino-ethoxy-ethyl)-amine, the following compounds were found in the mixture obtained by reacting N,N-2-dimethylamino-ethoxy-ethanol with ammonia:

bis(N,N-2-dimethylaminoethoxyethyl)amine

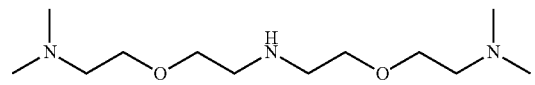

bis(N,N-2-dimethylaminoethoxyethyl)methylamine:

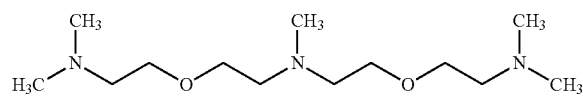

[2-(2-Dimethylamino-ethoxy)-ethyl]-[2-(2-methylamino-ethoxy)-ethyl]-amine or by UPAC nomenclature: 2,8,14-triaza-5,11-dioxa-2-methyl-pentadecane:

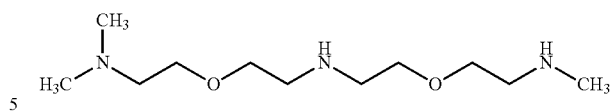

[2-(2-Amino-ethoxy)-ethyl]-[2-(2-dimethylamino-ethoxy)-ethyl]-methyl-amine or by UPAC nomenclature: 2,8,14-triaza-5,11-dioxa-2,8-dimethyl-tetradecane:

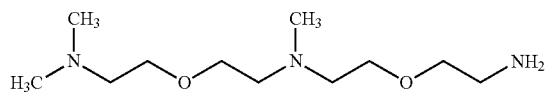

and [2-(2-{Bis-[2-(2-dimethylamino-ethoxy)-ethyl]-amino}-ethoxy)-ethyl]-dimethyl-amine, (also referred to as TM33); MW 362,

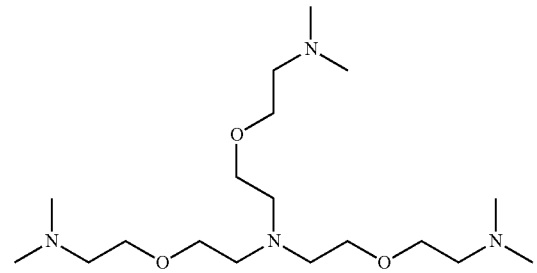

Identification was done by using GC/MS- and NMR spectroscopy.

A recycle of at least a part of the mixture obtained by reacting N,N-2-dimethylamino-ethoxy-ethanol with ammonia, in particular the middle and heavy fraction, more preferred the heavy fraction only, to the amination reactor, results in a decrease of the T22 concentration whereas the concentration of [2-(2-{Bis-[2-(2-dimethylamino-ethoxy)-ethyl]-amino}-ethoxy)-ethyl]-dimethyl-amine shows a significant increase. This material could be isolated by simple distillation as a single product.

In general, according to a second aspect of the present invention, a method for providing a tertiary amine with formula $(R^1R^2NR^3)_3N$ wherein each of $R^1$ and $R^2$ are chosen from the group consisting of a methyl group, an ethyl group, an iso-propyl group and an n-propyl group;

$R^3$ being an alkoxyalkyl group chosen from the group consisting of —CH$_2$CH$_2$OCH$_2$CH$_2$—, —CH$_2$CH$_2$OCH$_2$CH$_2$CH$_2$— and —CH$_2$CH$_2$CCH$_2$OCH$_2$CH$_2$CH$_2$—, is provided, wherein the method comprises the steps:

(1) reacting $R^1R^2NR^3(OH)$ with ammonia, thereby providing a mixture comprising $(R^1R^2NR^3)_2NH$ and $(R^1R^2NR^3)_3N$;

(2) recycle at least part of said mixture to the reaction of $R^1R^2NR^3(OH)$ with ammonia;

(3) separating $(R^1R^2NR^3)_3N$ from said mixture.

Hence, a method to provide a tertiary amine with formula $(R^1R^2NR^3)_3N$ is provided, the method comprising the additional step of recycling at least part of the mixture to the reaction of $R^1R^2NR^3(OH)$ with ammonia prior to separation of the amine, in this method the tertiary amine $(R^1R^2NR^3)_3N$ from said mixture, additional to the method according to the first aspect of the present invention.

As such, according to a further aspect of the present invention, a tertiary amine with formula $(R^1R^2NR^3)_3N$, wherein
each of $R^1$ and $R^2$ are a methyl group;
$R^3$ being —$CH_2CH_2OCH_2CH_2$—
is provided.

Further, according to an aspect of the present invention, $(R^1R^2NR^3)_3N$ obtained using to a method according to the present invention is provided.

In case the method according to the present invention aims to provide an amine with general formula $(R^1R^2NR^3)_2NH$, i.e. an amine according to the present invention wherein $R^4$ is hydrogen, the method may further comprise the step of separating and purifying $(R^1R^2NR^3)_2NH$ by
amidation of the mixture comprising $(R^1R^2NR^3)_2NH$, such as with a carboxylic acid, preferably formic acid, to provide an amidated mixture comprising the corresponding $(R^1R^2NR^3)_2NH$ based amide;
separating the $(R^1R^2NR^3)_2NH$ based amide from the other components of the amidated mixture;
recovering $(R^1R^2NR^3)_2NH$ from its amide by deamidation of the $(R^1R^2NR^3)_2NH$ based amide, optionally by transamidation or by hydrolysation using a basic component, preferably an inorganic basic component, most preferably NaOH or KOH.

The separation of the $(R^1R^2NR^3)_2NH$ based amide from the other components of the amidated mixture may be done by distillation.

The obtained $(R^1R^2NR^3)_2NH$, obtained using the method according to the first aspect of the present invention, typically has a purity of 98% or even more.

According to a third aspect of the present invention, an amine with formula $(R^1R^2NR^3)_2NH$ wherein
each of $R^1$ and $R^2$ are chosen from the group consisting of a methyl group, an ethyl group, an iso-propyl group and an n-propyl group;
$R^3$ being an alkoxyalkyl group chosen from the group consisting of —$CH_2CH_2OCH_2CH_2$—, —$CH_2CH_2OCH_2CH_2CH_2$— and —$CH_2CH_2CH_2OCH_2CH_2CH_2$—;
is provided, which amine is obtainable or is obtained according to a method of the first aspect of the present invention. This amine obtained according to the first aspect of the present invention may comprise alkylated, optionally $(R^1R^2NR^3)_2NR^1$, such as methylated, and/or transalkylated $(R^1R^2NR^3)_2NH$, optionally in a range of 0.1 to 20 w %, such as in the range of 1% w to 18% w, more preferred in the range of 2% w to 16% w.

More preferred, a secondary amine with formula $(R^1R^2NR^3)_2NH$ is provided, wherein
each of $R^1$ and $R^2$ are a methyl group;
$R^3$ being —$CH_2CH_2OCH_2CH_2$—.

This secondary amine is also referred to as bis(N,N-2-dimethylaminoethoxyethyl)amine.

This $(R^1R^2NR^3)_2NH$, wherein
each of $R^1$ and $R^2$ are a methyl group;
$R^3$ being —$CH_2CH_2OCH_2CH_2$—
may comprise alkylated $(R^1R^2NR^3)_2NH$, typically $(R^1R^2NR^3)_2NR^1$. The bis(N,N-2-dimethylaminoethoxyethyl)amine obtained typically comprises 80% w or more than 80% w bis(N,N-2-dimethylaminoethoxyethyl)amine and 0.1 to 20 w %, such as 1% w to 18% w, more preferred 2% w to 16% w of bis(N,N-2-dimethylaminoethoxyethyl)methylamine.

Optionally, $(R^1R^2NR^3)_2NH$ according to the present invention is bis(N,N-2-dimethylaminoethoxyethyl)amine.

According to a fourth aspect of the present invention, a method for providing a tertiary amine with formula $(R^1R^2NR^3)_2NR^4$, wherein $R^4$ is chosen from the group consisting of a methyl group, an ethyl group, an iso-propyl group and an n-propyl group I provided. The method comprises the steps:
(1) providing $(R^1R^2NR^3)_2NH$ using the method according to the first aspect of the present invention;
(2) converting said $(R^1R^2NR^3)_2NH$ into $(R^1R^2NR^3)_2NR^4$ by alkylation of $(R^1R^2NR^3)_2NH$.

Hence a method to provide a tertiary amine with formula $(R^1R^2NR^3)_2NR^4$, $R^4$ being chosen from the group consisting of a methyl group, an ethyl group, an iso-propyl group and an n-propyl group is provided, the method comprising the additional step of converting said $(R^1R^2NR^3)_2NH$ into $(R^1R^2NR^3)_2NR^4$ by alkylation of $(R^1R^2NR^3)_2NH$, additional to and consecutive to the steps of a method according to the first aspect of the present invention.

According to a fifth aspect of the present invention, a method for providing a tertiary amine with formula $(R^1R^2NR^3)_2NR^4$, wherein $R^4$ is chosen from the group consisting of a methyl group, an ethyl group, an iso-propyl group and an n-propyl group is provided. The method comprises the steps:
(1) reacting $R^1R^2NR^3(OH)$ with ammonia, thereby providing a mixture comprising $(R^1R^2NR^3)_2NH$;
(2) alkylating said mixture comprising said $(R^1R^2NR^3)_2NH$ into an alkylated mixture comprising $(R^1R^2NR^3)_2NR^4$;
(3) separating $(R^1R^2NR^3)_2NR^4$ from said alkylated mixture.

These methods have the advantage that simultaneously, alkylated compounds based upon alkylation of $(R^1R^2NR^3)NH_2$ are provided.

Hence a method may be a method according to the fourth aspect of the present invention, the method comprising the additional step of separating $(R^1R^2NR^3)_2NR^4$ from said alkylated mixture.

According to a sixth aspect of the present invention, $(R^1R^2NR^3)_2NR^4$ obtained according to a method of the fourth or the fifth aspect of the invention is provided, wherein
each of $R^1$ and $R^2$ are chosen from the group consisting of a methyl group, an ethyl group, an iso-propyl group and an n-propyl group;
$R^3$ being an alkoxyalkyl group chosen from the group consisting of —$CH_2CH_2OCH_2CH_2$—, —$CH_2CH_2OCH_2CH_2CH_2$— and —$CH_2CH_2CH_2OCH_2CH_2CH_2$—;
$R^4$ is chosen from the group consisting of a methyl group, an ethyl group, an iso-propyl group and an n-propyl group,
said $(R^1R^2NR^3)_2NR^4$ is substantially free of chlorine.

Substantially free of chlorine is to be understood as comprising less than 0.01 w % of Cl in free or bound form.

In case N,N-2-dimethylaminoethoxyethanol is reacted with ammonia, a mixture comprising bis(N,N-2-dimethylaminoethoxyethyl)amine and at least one of N,N-2-dimethylaminoethoxyethylamine, N,N-2-dimethylaminoethoxyethylmethylamine, and/or N,N-2-dimethylaminoethoxyethyldimethylamine is provided. By methylation of this mixture, an alkylated, i.e. methylated mixture is provided substantially consisting of bis(N,N-2-dimethylaminoethoxyethyl)methylamine and N,N-2-dimethylaminoethoxyethyldimethylamine. By simple distillation, substantially pure bis(N,N-2-dimethylaminoethoxyethyl)methylamine and N,N-2- dimethylaminoethoxyethyldimethylamine can be provided. Both products may have a purity of more than 99 w %.

Alkylation can e.g. be methylation by catalytically reacting bis(N,N-2-dialkylaminoalkoxyalkyl)amine with formaldehyde in presence of hydrogen. It can e.g. by ethylation by catalytically reacting bis(N,N-2-dialkylaminoalkoxyalkyl) amine with acetaldehyde in presence of hydrogen.

In the amines with formula $(R^1R^2NR^3)_2NR^4$ according to the present invention, $R^4$ is preferably identical to $R^1$ and $R^2$. In particular, when $(R^1R^2NR^3)_2NH$ as starting or intermediate being bis-(N,N-2-dimethyl-aminoethoxyethyl)amine, $R^4$ is methyl, whereby bis-(N,N-2-dimethyl-aminoethoxyethyl)methylamine (hereinafter TM22) is provided. The obtained bis-(N,N-2-dimethyl-aminoethoxyethyl)methylamine typically may comprise incomplete alkylated, such as methylated bis-(N,N-2-dimethyl-aminoethoxyethyl)methylamine.

Regarding bis-(N,N-2-dimethyl-aminoethoxyethyl)methylamine, the bis-(N,N-2-dimethyl-aminoethoxyethyl)methylamine obtained using a method according to the present invention is substantially free of Cl, S, P and Na, as is not the case for bis-(N,N-2-dimethyl-aminoethoxyethyl)methylamine prepared using the process of DE2618280.

The purity of the bis-(N,N-2-dimethyl-aminoethoxyethyl)methylamine obtainable by the methods according to the present invention, may be up to 99 w %, even up to above 99 w %. The bis-(N,N-2-dimethyl-aminoethoxyethyl)methylamine provided according to the present invention may further comprise impurities being [2-(2-Dimethylamino-ethoxy)-ethyl]-[2-(2-methylamino-ethoxy)-ethyl]-amine or by UPAC nomenclature: 2,8,14-triaza-5,11-dioxa-2-methyl-pentadecane (possibly in an amount of less than 0.1 w %) and/or [2-(2-Amino-ethoxy)-ethyl]-[2-(2-dimethylamino-ethoxy)-ethyl]-amine or by UPAC nomenclature: 2,8,14-triaza-5,11-dioxa-2,8-dimethyl-tetradecane; MW 233 (possibly in an amount of less than 0.1 w %).

Other unknown high boiling components may be present in an amount of less than 0.1 w %.

According to some embodiments of the present invention, the purity of the bis-(N,N-2-dimethyl-aminoethoxyethyl)methylamine in particular, and $(R^1R^2NR^3)_2NR^4$ obtained according to a method of the fourth or the fifth aspect of the invention in general, wherein
each of $R^1$ and $R^2$ are chosen from the group consisting of a methyl group, an ethyl group, an iso-propyl group and an n-propyl group;
$R^3$ being an alkoxyalkyl group chosen from the group consisting of $-CH_2CH_2OCH_2CH_2-$, $-CH_2CH_2OCH_2CH_2CH_2-$ and $-CH_2CH_2CH_2OCH_2CH_2CH_2-$;
$R^4$ is chosen from the group consisting of a methyl group, an ethyl group, an iso-propyl group and an n-propyl group,
may be more than 95 w %, optionally above 99 w %.

According to some embodiments of the present invention, $(R^1R^2NR^3)_2NR^4$ obtained according to a method of the fourth or the fifth aspect of the invention is provided, wherein
each of $R^1$ and $R^2$ are chosen from the group consisting of a methyl group, an ethyl group, an iso-propyl group and an n-propyl group;
$R^3$ being an alkoxyalkyl group chosen from the group consisting of $-CH_2CH_2OCH_2CH_2$, $-CH_2CH_2OCH_2CH_2CH_2-$ and $-CH_2CH_2CH_2OCH_2CH_2CH_2-$;
$R^4$ is chosen from the group consisting of a methyl group, an ethyl group, an iso-propyl group and an n-propyl group
may comprise impurities being $(R^1R^2NR^3)_2NH$.

According to some embodiments of the present invention, $R^1$, $R^2$ and $R^4$ are methyl and $R^3$ is $-CH_2CH_2OCH_2CH_2-$.

The obtainable or obtained amine with formula $(R^1R^2NR^3)_2NR^4$ wherein
each of $R^1$ and $R^2$ are chosen from the group consisting of a methyl group, an ethyl group, an iso-propyl group and an n-propyl group;
$R^3$ being an alkoxyalkyl group chosen from the group consisting of $-CH_2CH_2OCH_2CH_2-$, $-CH_2CH_2OCH_2CH_2CH_2-$ and $-CH_2CH_2CH_2OCH_2CH_2CH_2-$;
$R^4$ is chosen from the group consisting of a hydrogen, a methyl group, an ethyl group, an iso-propyl group, an n-propyl group and a group with formula $R^1R^2NR^3$,
in particular bis(N,N-2-dimethylaminoethoxyethyl)amine and bis(N,N-2-dimethylaminoethoxyethyl)methylamine, may be used as catalyst for catalysation of the reaction of isocyanate with compounds comprising isocyanate reactive groups such as alcohols and amines. Typically they may be used as catalyst in the provision of polyurethane, e.g. rigid or flexible polyurethane foam, or polyurethane elastomers or adhesives.

According to a further aspect of the present invention, bis(N,N-2-dimethylaminoethoxyethyl)amine obtainable or obtained according to the present invention is used as catalyst in the reaction of isocyanates and isocyanate reactive compounds for providing polyurethane.

Bis(N,N-2-dimethylaminoethoxyethyl)methylamine obtainable or obtained according to the present invention may also be used as catalyst in the reaction of isocyanates and isocyanate reactive compounds for providing polyurethane.

The independent and dependent claims set out particular and preferred features of the invention. Features from the dependent claims may be combined with features of the independent or other dependent claims as appropriate.

The above and other characteristics, features and advantages of the present invention will become apparent from the following detailed description, which illustrate, by way of example, the principles of the invention. This description is given for the sake of example only, without limiting the scope of the invention.

The present invention will be described with respect to particular embodiments.

It is to be noticed that the term "comprising", used in the claims, should not be interpreted as being restricted to the means listed thereafter; it does not exclude other elements or steps. It is thus to be interpreted as specifying the presence of the stated features, steps or components as referred to, but does not preclude the presence or addition of one or more other features, steps or components, or groups thereof. Thus, the scope of the expression "a device comprising means A and B" should not be limited to devices consisting only of components A and B. It means that with respect to the present invention, the only relevant components of the device are A and B.

Throughout this specification, reference to "one embodiment" or "an embodiment" are made. Such references indicate that a particular feature, described in relation to the embodiment is included in at least one embodiment of the present invention. Thus, appearances of the phrases "in one embodiment" or "in an embodiment" in various places throughout this specification are not necessarily all referring to the same embodiment, though they could. Furthermore, the particular features or characteristics may be combined in any suitable manner in one or more embodiments, as would be apparent to one of ordinary skill in the art from this disclosure.

The following terms are provided solely to aid in the understanding of the invention.

When reference is made to boiling points or boiling temperature, unless otherwise indicated, the boiling point or boiling temperature indicates the boiling point or boiling temperature under atmospheric pressure.

Unless otherwise indicated, any percentage of a component refers to weight percentages over the total weight of the substance in which the individual component is present.

The various aspects of the present invention will further be described in detail by means of one or more examples relating to the separation of Bis-(N,N-2-dimethylaminoethoxyethyl)amine from a mixture further comprising N,N-dimethyl-bisaminoethylether (T2MBAEE), N,N,N'-trimethylbisaminoethylether (T3MBAEE), and/or N,N,N',N'-tetramethylbisaminoethylether (T4MBAEE) as well as the provision of alkylated Bis-(N,N-2-dimethylaminoethoxyethyl)amine such as in particular Bis-(N,N-2-dimethylaminoethoxyethyl)methylamine, and [2-(2-{Bis-[2-(2-dimethylamino-ethoxy)-ethyl]-amino}-ethoxy)-ethyl]-dimethyl-amine.

The skilled person however understands that the same principle applies for secondary amines with formula $(R^1R^2NR^3)_2NH$ wherein
each of $R^1$ and $R^2$ and are chosen from the group consisting of a methyl group, an ethyl group, an iso-propyl group or an n-propyl group;
$R^3$ being an alkoxyalkyl group chosen from the group consisting of $-CH_2CH_2OCH_2CH_2-$, $-CH_2CH_2OCH_2CH_2CH_2-$ and $-CH_2CH_2CCH_2OCH_2CH_2CH_2-$,
and for tertiary amines with formula $(R^1R^2NR^3)_2NR^4$ wherein
each of $R^1$ and $R^2$ are chosen from the group consisting of a methyl group, an ethyl group, an iso-propyl group and an n-propyl group;
$R^3$ being an alkoxyalkyl group chosen from the group consisting of $-CH_2CH_2OCH_2CH_2-$, $-CH_2CH_2OCH_2CH_2CH_2-$ and $-CH_2CH_2CH_2OCH_2CH_2CH_2-$;
$R^4$ is chosen from the group consisting of a hydrogen, a methyl group, an ethyl group, an iso-propyl group, an n-propyl group and a group with formula $R^1R^2NR^3$.

According to an aspect of the present invention, N,N-2-dimethylaminoethoxyethylamine, (also referred to as N,N-dimethylaminoethoxyethylamine, T2 or T2MBAEE), was synthesized by reacting N,N-2-dimethyl-aminoethoxyethanol with ammonia over a copper-chromite catalyst. The reaction scheme looks like:

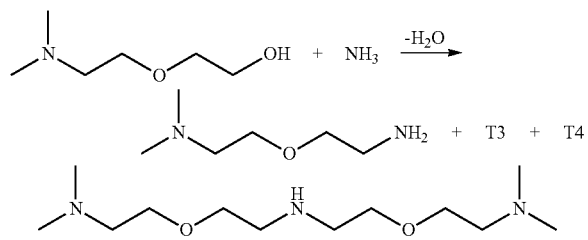

Wherein T3 refers to N,N,N'-trimethylbisaminoethylether (or T3MBAEE) and wherein T4 refers to N,N,N',N'-tetramethylbisaminoethylether (also known as T4MBAEE or JEFFCAT® ZF-20). N,N-2-dimethyl-aminoethoxyethanol is also known as JEFFCAT® ZR-70.

In the reactor effluent the following materials were identified:

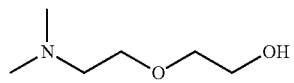

N,N-2-dimethylaminoethoxyethanol

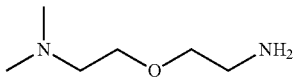

N,N-2-dimethyaminoethoxyethylamine (also referred to as T2)

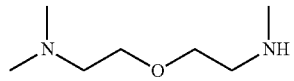

N,N,N'-trimethylbisaminoethylether (also referred to as T3) and

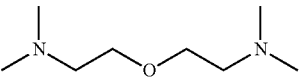

N,N,N',N'-tetramethylbisaminoethylether (also referred to as T4).

Also, a dimerized form of T2 was detected in the reactor effluent as a main component, which is:

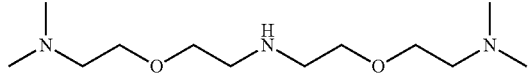

Bis-(N,N-2-dimethylaminoethoxyethyl)amine (hereinafter also referred to as "T22" or "T2-dimer"), molecular weight (hereinafter MW) 247.

Further other components were identified as various compounds structurally similar to bis-(N,N-2-dimethylamino-ethoxy-ethyl)-amine, e.g. the methylated derivative of N,N-bis(2-aminoethoxyethyl-)amine, having the structure:

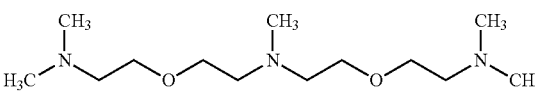

i.e. bis-(N,N-2-dimethylaminoethoxyethyl-1)methylamine (also referred to as "TM22") or by UPAC nomenclature: 2,8,14-triaza-5,11-dioxa-2,8,14-trimethyl-pentadecane), MW 261.

Further components having a similar structure as T22 are

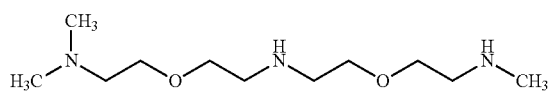

[2-(2-Dimethylamino-ethoxy)-ethyl]-[2-(2-methylamino-ethoxy)-ethyl]-amine or by UPAC nomenclature: 2,8,14-triaza-5,11-dioxa-2-methyl-pentadecane, MW 233, and

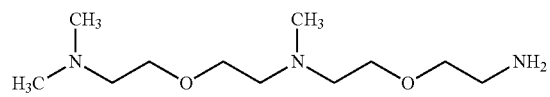

[2-(2-Amino-ethoxy)-ethyl]-[2-(2-dimethylamino-ethoxy)-ethyl]-methyl-amine or by UPAC nomenclature: 2,8,14-triaza-5,11-dioxa-2,8-dimethyl-tetradecane; MW 233, and some minor amount of

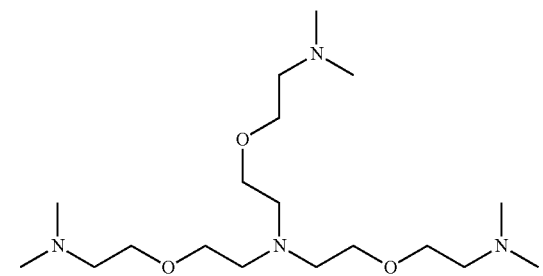

[2-(2-{Bis-[2-(2-dimethylamino-ethoxy)-ethyl]-amino}-ethoxy)-ethyl]-dimethyl-amine; MW 362.

The reactor effluent was split by distillation into three fractions:
- a light fraction, essentially consisting of water and morpholines.
- a middle fraction containing N,N-2-dimethylaminoethoxyethylamine, N,N,N'-trimethylbisaminoethylether, N,N,N',N'-tetramethylbisaminoethylether and N,N-2-dimethylaminoethoxyethanol, and
- a heavy fraction consisting mainly of bis-(N,N-2-dimethylaminoethoxyethyl)amine and the other by-products.

In the middle fraction the products T2, T3 and T4 were found, whereas in the heavy fraction bis-(N,N-2-dimethylaminoethoxyethyl)amine is contained by ca. 85 wt.-% (w % over total weight of heavy fraction). Two other by-products (in total ca. 15 wt.-%) were found in that material. According to GC/MS analysis these materials are having very similar structures as T22.

Depending on the reaction conditions of the amination of N,N-2-dimethylaminoethoxyethanol with ammonia, a wide range of ratios of T2/T3/T4 may be obtained in the middle fraction. In all experiments done, T2/T3/T4 were present. As an example the ratio T2/T3/T4 can be 3.6/1/1.3.

Example 1

Provision of T2/T3/T4/T22 Mixture by Reacting dimethylaminoethoxyethanol with Ammonia A 1000 ml stainless steel reactor was charged with 2000 g commercial 2CuOxCr$_2$O$_3$ catalyst (CAS#99328-50-4, from Aldrich). The head of the continuous reactor system was connected with separate inlet lines and feed pumps for liquid ammonia and dimethylaminoethoxyethanol.

Ammonia and N,N-2-dimethylaminoethoxyethanol were charged to the reactor at different reaction conditions, as shown in Table 1. The reactor effluents were taken off at the bottom of the reactor, depressurized, degassed and collected for analysis and further use. All running conditions and compositions of the reactor effluents are shown in Table 1.

TABLE 1

Running conditions and product composition

| Reaction conditions | unit | Run 1 | Run 2 | Run 3 | Run 4 | Run 5 |
|---|---|---|---|---|---|---|
| Reactor temperature | °C. | 170 | 180 | 190 | 200 | 170 |
| Reactor pressure | bar | 70 | 70 | 70 | 70 | 70 |
| Catalyst load | | | | | | |
| ammonia | ltr/h | 0.1 | 0.1 | 0.1 | 0.1 | 0.1 |
| N,N-2-dimethylamino-ethoxyethanol | ltr/h | 0.5 | 0.5 | 0.5 | 0.5 | 0.13 |
| Mol ratio ammonia versus N,N-2-dimethylamino-ethoxyethanol | | 1.6:1 | 1.6:1 | 1.6:1 | 1.6:1 | 6:1 |

| Product composition [wt.-%] | | | | | | |
|---|---|---|---|---|---|---|
| Compound | | Run 1 | Run 2 | Run 3 | Run 4 | Run 5 |
| morpholine | [wt.-%] | 0.18 | 0.53 | 0.79 | 1.12 | 0.37 |
| N-methylmorpholine | [wt.-%] | 0.26 | 0.70 | 1.16 | 1.89 | 0.30 |
| N,N-2-dimethylamino-ethoxyethylamine | [wt.-%] | 6.63 | 6.61 | 8.60 | 7.96 | 13.88 |
| N,N,N'-trimethylbisamino-ethylether | [wt.-%] | 0.38 | 0.95 | 1.69 | 2.31 | 0.08 |
| N,N,N',N'-tetramethylbisamino-ethylether | [wt.-%] | 0.52 | 1.71 | 1.80 | 2.71 | 0.40 |
| N,N-2-dimethylamino-ethoxyethanol | [wt.-%] | 79.32 | 67.34 | 52.92 | 47.23 | 51.48 |
| bis-(N,N-2-dimethylamino-ethoxyethyl)amine | [wt.-%] | 9.25 | 13.18 | 20.82 | 21.14 | 25.60 |
| compounds structurally similar to bis-(N,N-2-dimethylamino-ethoxy-ethyl)-amine | [wt.-%] | 3.64 | 8.98 | 12.22 | 15.64 | 7.12 |

All reactor effluents were combined (resulting in 8500 g crude material) and fractioned on a batch-type distillation tower, containing structured packings, having a total packing length of 100 cm. A main split was carried out to divide the combined reactor effluents in to three fractions. Fraction#1 and fraction#2 were collected as overhead products, whereas fraction#3 was taken as the residue stream.

Fraction#1 was containing all reaction water and various light boiling components like morpholine, N-methylmorpholine and others. Fraction#2 contained mainly N,N-2-dimethylaminoethoxyethylamine, N,N,N'-trimethylbisaminoethylether, N,N,N',N'-tetramethylbisaminoethylether, and N,N-2-dimethyl-aminoethoxyethanol. Working conditions and results of the main split distillation are shown in Table 2.

TABLE 2

Conditions and results of main splitting distillation forming fractions #1 and fraction #2

|  | unit | fraction #1, Example 1 | fraction #2, Example 1 |
|---|---|---|---|
| Boiling range, head temperature | ° C. | 48-98 | 98-133 |
| Boiling range, pot temperature | ° C. | 92-143 | 143-145 |
| Pressure | mbar | 100 | 100 |
| Reflux:take off ratio (vapour divider) |  | 05:01 | 15:01 |
| product composition [wt.-%] *) |  |  |  |
| morpholine | [wt.-%] | nd | 0.43 |
| N-methylmorpholine | [wt.-%] | nd | 0.22 |
| N,N-2-dimethylaminoethoxyethylamine (=A) | [wt.-%] | nd | 40.07 |
| N,N,N'-trimethylbis-aminoethylether (=B) | [wt.-%] | nd | 11.01 |
| N,N,N',N'-tetramethylbisaminoethylether (=C) | [wt.-%] | nd | 14.70 |
| N,N-2-dimethylaminoethoxyethanol | [wt.-%] | nd | 29.51 |
| bis-(N,N-2-dimethylaminoethoxyethyl)amine | [wt.-%] | nd | 0.01 |
| other components | [wt.-%] | nd | 4.05 |
| Ratio A:B:C |  | nd | 40:11:15 |

*) = based on water free material
nd = not determined

The bottom fractions were retained as residue fraction#3. GC-analysis of this residue-fraction#3, showed that it consists mainly of bis-(N,N-2-dimethylaminoethoxyethyl)amine and some other components. Further examination and analysis showed that these other components are structurally similar to bis-(N,N-2-dimethylaminoethoxyethyl)amine, some being identified as

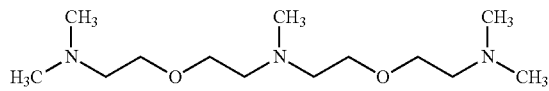

bis-(N,N-2-dimethylaminoethoxyethyl-1)methylamine (also referred to as "TM22") or by UPAC nomenclature: 2,8,14-triaza-5,11-dioxa-2,8,14-trimethyl-pentadecane), MW 261, and

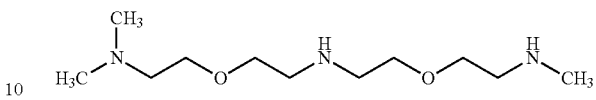

[2-(2-Dimethylamino-ethoxy)-ethyl]-[2-(2-methylamino-ethoxy)-ethyl]-amine or by UPAC nomenclature: 2,8,14-triaza-5,11-dioxa-2-methyl-pentadecane.

There are indications that another trace-impurity in T22 is

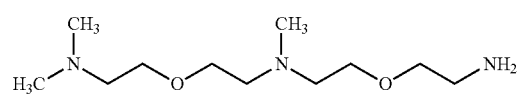 [SMILES: CN(C)CCOCCN(C)CCOCCN]

[2-(2-Amino-ethoxy)-ethyl]-[2-(2-dimethylamino-ethoxy)-ethyl]-methyl-amine or by UPAC nomenclature: 2,8,14-triaza-5,11-dioxa-2,8-dimethyl-tetradecane; MW 233.

Also some [2-(2-{Bis-[2-(2-dimethylamino-ethoxy)-ethyl]-amino}-ethoxy)-ethyl]-dimethyl-amine was identified.

This heavy fraction was distilled at different vacuum- and temperature conditions on a batch-type distillation tower, containing structured packing, having a total packing length of 100 cm. After a short transition fraction, fraction#4, two product fractions, fraction#5 and fraction#6 were taken.

Working conditions and results of distillation of residue-fraction#3 are shown in Table 3.

TABLE 3 conditions and results of distillation of residue-fraction #3

|  | unit | Example 1, fraction #4 | Example 1, fraction #5 | Example 1, fraction #6 |
|---|---|---|---|---|
| Boiling range, head temperature | ° C. | 20-20 | 120-125 | 125-128 |
| Boiling range, pot temperature | ° C. | 20-120 | 169-174 | 174-175 |
| Pressure | mbar | 7 | 7 | 7 |
| Reflux:take off ratio (vapour divider) |  | 2:1 | 2:1 | 2:1 |
| product composition [wt.-%] *) | [wt.-%] | Example 1, fraction #4 | Example 1, fraction #5 | Example 1, fraction #6 |
| morpholine | [wt.-%] | nd | 0 | 0 |
| N-methylmorpholine | [wt.-%] | nd | 0 | 0 |
| N,N-2-dimethylaminoethoxyethylamine (=A) | [wt.-%] | nd | 0 | 0 |
| N,N,N'-trimethylbis-aminoethylether (=B) | [wt.-%] | nd | 0 | 0 |
| N,N,N',N'-tetramethylbisaminoethylether (=C) | [wt.-%] | nd | 0 | 0 |
| N,N-2-dimethylaminoethoxyethanol | [wt.-%] | nd | 0.17 | 0.01 |
| bis-(N,N-2-dimethylaminoethoxyethyl)amine | [wt.-%] | nd | 83.83 | 81.02 |
| compounds structurally similar to bis-(N,N-2-dimethylamino-ethoxy-ethyl)-amine | [wt.-%] | nd | 16.0 | 18.97 |

*) = based on water free material
nd = not determined 868 g of fracton#5/Example1 was filled in to a 2 liter distillation flask of a batch type distillation tower containing structured packing's (packing length=1 m).

A careful fractionation resulted 470.2 g of a product (fine fraction #2 in table 4) containing 87.7 wt.-% bis-(N,N-2-dimethyl-aminoethoxyethyl)amine ("T2dimer" or "T22"). Conditions and results are shown in Table 4.

TABLE 4

Conditions and results of fine fractionation of fraction #5/Example 1

|  | unit | Fine fraction #1, | Fine fraction #2, |
|---|---|---|---|
| Boiling range, head temperature | ° C. | 150-151 | 151-152 |
| Boiling range, pot temperature | ° C. | 173-174 | 174 |
| Pressure | mbar | 7 | 7 |
| Reflux:take off ratio (vapour divider) |  | 20:01 | 20:01 |

| product composition [wt.-%] *) | [wt.-%] | Fine fraction #1, | Fine fraction #2, |
|---|---|---|---|
| N,N-2-dimethyl-aminoethoxyethanol | [wt.-%] | nd | 0 |
| bis-(N,N-2-dimethylaminoethoxyethyl)amine | [wt.-%] | nd | 87.73 |
| bis-(N,N-2-dimethylaminoethoxyethyl)methylamine | [wt.-%] | nd | 8.81 |
| [2-(2-Amino-ethoxy)-ethyl]-[2-(2-dimethylamino-ethoxy)-ethyl]-methyl-amine | [wt.-%] | nd | 3.46 |

*) = based on water free material
nd = not determined

The structure of bis-(N,N-2-dimethyl-aminoethoxyethyl) amine was verified by GC/MS spectroscopy. The other components were identified as structural isomer of bis-(N,N-2-dimethylamino-ethoxy-ethyl)-amine or compounds structurally similar to bis-(N,N-2-dimethylamino-ethoxy-ethyl)-amine.

A boiling point of 300° C. is estimated for bis-(N,N-2-dimethylamino-ethoxy-ethyl)-amine. A boiling point of 150-152° C. at 7 mbar vacuum is measured To separate and refine T22 from this mixture, the fractions #5 and/or #6 of example 1 were reacted with formic acid.

TM22 could not react with the formic acid

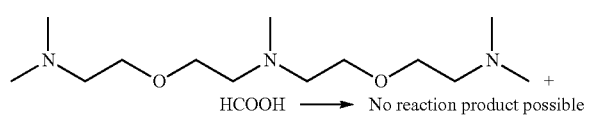

HCOOH ⟶ No reaction product possible

Following reactions occurred:

Reaction 1

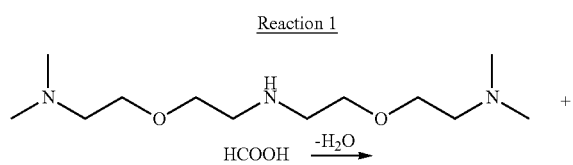

HCOOH $\xrightarrow{-H_2O}$

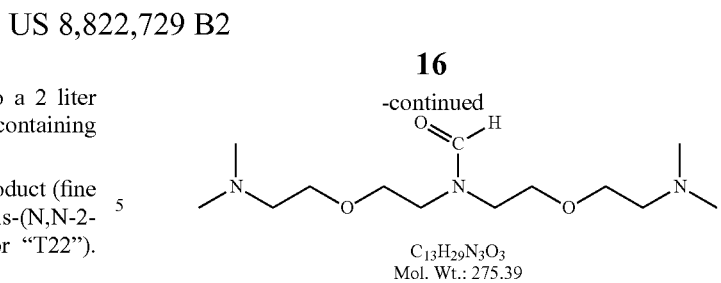

$C_{13}H_{29}N_3O_3$
Mol. Wt.: 275.39
N,N-Bis-[2-(2-dimethylamino-ethoxy)-ethyl]-formamide Reaction 2

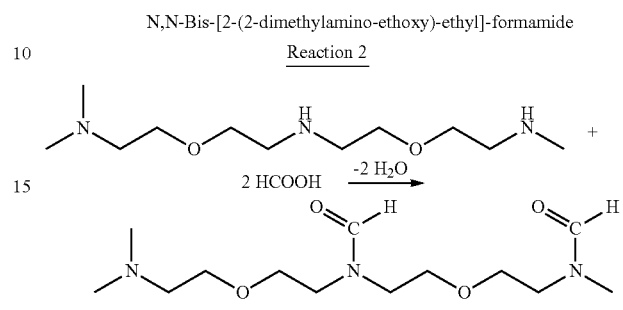

It can be easily seen from these reactions, that TM22 does not form any formylation product. T22 is providing by such a formylation reaction and by addition of one formyl group a mono formamide, namely N,N-Bis-[2-(2-dimethylamino-ethoxy)-ethyl]-formamide (reaction 1), whereas the formylation reaction shown by reaction 2 is resulting a product having two formyl groups in the molecule. A result of this measure is a large differentiation of the boiling points of TM22 and the formed formamides. By a simple vacuum distillation, optionally even without utilizing a fractionation tower, TM22 appears as a "light end component". The N,N-bis-[2-(2-dimethylamino-ethoxy)-ethyl]-formamide is forming the main fraction, having a purity of 98% or more (the remainder being impurities due to the reaction steps as described above), whereas the other formamide as shown in reaction 2 is remaining in the distillation residue due to the difference of its boiling point with the N,N-Bis-[2-(2-dimethylamino-ethoxy)-ethyl]-formamide.

Subsequent deformylation of the N,N-bis-[2-(2-dimethylamino-ethoxy)-ethyl]-formamide provides T22 in good yield and appreciable purity. Such a deformylation reaction can be carried out under acidic or alkalinic reaction condition. In the following reaction 3 alkalinic conditions were chosen using e.g. potassium hydroxide.

Reaction 3

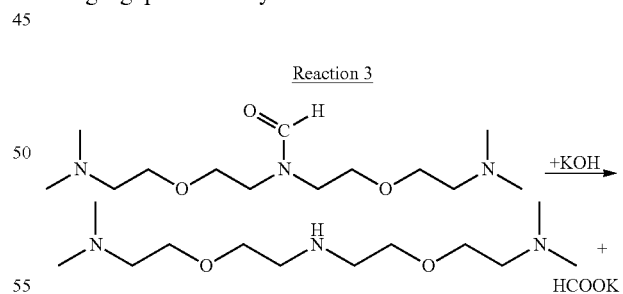

Example 2

Manufacture of bis-(N,N-2-dimethylaminoethoxyethyl-1)methylamine (Also Called "TM22") by methylation, Starting from Fine Fraction #2 of Example 1 and formaldehyde In a further step, the fine fraction #2 of example 1 was further alkylated, in particular methylated.

Low-pressure Reaction:

270 g "T2-dimer" (fine fraction #2 of example 1) were dissolved in 270 g methanol. To this mixture a solution of 46 g paraformaldehyde in 58 g methanol was slowly added. The temperature during the addition reaction was maintained at 40° C. After completion of the paraformaldehyde addition the reaction was for additional two hours stirred and thereafter allowed to cool down to ambient temperature.

High Pressure Hydrogenation:

The mixture prepared in the low-pressure reaction was hydrogenated over a Pd/C catalyst (1% Palladium supported on charcoal, filled in a 100 ml continuous reactor), at a hydrogen-pressure of 70 bar at 110° C.

Purification

The reactor effluent from hydrogenation was worked up in a simple laboratory distillation apparatus, consisting of a distillation flask, a Liebig condenser and a receiver without any distillation column.

TABLE 5

|  | unit | Example 2, fraction #1 | Example 2, fraction #2 | Example 2, fraction #3 | Example 2, fraction #4 |
|---|---|---|---|---|---|
| Boiling range, head temperature | ° C. | 20-100 | 47 | to 114 | 149 |
| Boiling range, pot temperature | ° C. | 20-145 | 165 | to 152 | 152 |
| Pressure | mbar | 1013 | 100 | 6 | 6 |
| Reflux:take off ratio (vapour divider) |  | non | non | non | non |

| product composition [wt.-%] *) | [wt.-%] | Example 2, fraction #1 | Example 2, fraction #2 | Example 2, fraction #3 | Example 2, fraction #4 |
|---|---|---|---|---|---|
| Water and methanol | [wt.-%] | nd | nd | nd | 0 |
| Interim fraction 1 | [wt.-%] | nd | nd | nd | 0 |
| Interim fraction 2 | [wt.-%] | nd | nd | nd | 0 |
| bis-(N,N-2-dimethylamino-ethoxyethyl-)methylamine ("TM22") | [wt.-%] | nd | nd | nd | 99.3 |
| others | [wt.-%] | nd | nd | nd | 0.7 |

*) = based on water free material
nd = not determined

Fraction #4 of this distillation resulted 200, 1 g of a product which was by GC and GC-MS analysis identified as bis-(N,N-2-dimethylaminoethoxyethyl-) methylamine ("TM22"), having a purity of 99.3 wt.-%. The fractions #1 and #2 were containing mainly methanol, whereas fraction #3 was a small interim fraction. As residue remained in this distillation flask remained 5.5 g.

Further analytical results of Example 2, fraction #4 are water content of 0.03% measured by KF titration, a formaldehyde content of substantially 0, a colour of 96 measured using Pt/Co and an appearance of a mobile liquid, substantially free of foreign matter, almost odourless and without the amine-typical smell It was found that substantially all bis-(N,N-2-dimethyl-aminoethoxyethyl)amine, as well as the compounds structurally similar to bis-(N,N-2-dimethylamino-ethoxy-ethyl)-amine, were methylated into bis-(N,N-2-dimethyl-aminoethoxyethyl)methylamine, hereinafter TM22.

The bis-(N,N-2-dimethyl-aminoethoxyethyl)methylamine obtained is substantially free of S (sulphur), P (phosphor), Cl (chlorine) and Na (Sodium).

It is understood that also this methylation can be performed using the residue fraction#3, or fraction 6 of example 1, or fraction #5 of example 1.

The purity of the bis-(N,N-2-dimethyl-aminoethoxyethyl)methylamine obtainable by the methods according to the present invention, may be up to 98 w %, even up to above 99 w %. Further impurities found were [2-(2-Amino-ethoxy)-ethyl]-[2-(2-dimethylamino-ethoxy)-ethyl]-methyl-amine (or by UPAC nomenclature: 2,8,14-triaza-5,11-dioxa-2,8-dimethyl-tetradecane; MW 233), [2-(2-Dimethylamino-ethoxy)-ethyl]-[2-(2-methylamino-ethoxy)-ethyl]-amine (or by UPAC nomenclature: 2,8,14-triaza-5,11-dioxa-2-methyl-pentadecane) or T22. Each of the impurities was present in an amount les than 0.5 w %

A boiling point of 300° C. is estimated for bis-(N,N-2-dimethylamino-ethoxy-ethyl)methylamine. A boiling point of 150-152° C. at 7 mbar vacuum is measured.

In an other method according to the invention, the fraction 5 was further refined and bis-(N,N-2-dimethyl-aminoethoxy-ethyl)amine was separated from the other bis-(N,N-2-dimethyl-aminoethoxyethyl)amine isomers, by distillation. To remove the light fraction, the temperature of the mixture in the reactor may be chosen in the range of 173-175° C., the temperature of the head of the column may be chosen in the range of 150-151° C. The pressure can be 7 mbar. To remove the middle fraction, the temperature of the mixture in the reactor may be chosen in the range of 174-175° C., the temperature of the head of the column may be chosen in the range of 151-152° C. The pressure may be 7 mbar. The column may comprise of 15-30 trays of structured packing.

Substantially pure bis-(N,N-2-dimethyl-aminoethoxy-ethyl)amine was obtained, i.e. bis-(N,N-2-dimethyl-aminoethoxyethyl)amine with a purity of 87 w %. Remaining compounds are bis-(N,N-2-dimethylaminoethoxyethyl-1) methylamine (also referred to as "TM22") or by UPAC nomenclature: 2,8,14-triaza-5,11-dioxa-2,8,14-trimethyl-pentadecane), MW 261 (0.1-18 w %) and [2-(2-Dimethylamino-ethoxy)-ethyl]-[2-(2-methylamino-ethoxy)-ethyl]-amine or by UPAC nomenclature: 2,8,14-triaza-5,11-dioxa-2-methyl-pentadecane (0.1-18 w %) and [2-(2-Amino-ethoxy)-ethyl]-[2-(2-dimethylamino-ethoxy)-ethyl]-methyl-amine or by UPAC nomenclature: 2,8,14-triaza-5,11-dioxa-2,8-dimethyl-tetradecane; MW 233 (0.1-18 w %). Some other unknown high boiling components may be present.

It is understood that this refining step can be followed by further alkylation such as methylation, as set out above.

It was found that the secondary amine with formula $(R^1R^2NR^3)_2NH$, wherein each of $R^1$ and $R^2$ are a methyl group;
$R^3$ being —$CH_2CH_2OCH_2CH_2$—, also referred to as bis-(N,N-2-dimethylamino-ethoxy-ethyl)-amine, can be used as a catalyst for reacting an isocyanate, more particular a polyisocyanate with isocyanate reactive compounds, such as polyols or polyamines or water, in formulations where the similar product bis-(N,N-2-dimethyl-aminoethoxyethyl)methylamine fails.

As an example, a packaging PU-foam formulation as set out hereinafter was reacted using bis-(N,N-2-dimethy-lamino-ethoxy-ethyl)-amine (formulation I) or bis-(N,N-2-dimethyl-aminoethoxyethyl)methylamine (formulation II) as catalyst.

TABLE 6

| formulation | Amount (gram) |
|---|---|
| Jeffsol SG-522 | 45 |
| G 31-28 | 45 |
| Surfonic N-95 | 10 |
| water | 40 |
| Tegostab B-8870 | 2.8 |
| Rubinate M | 200 |
| catalyst | 2.7 |

Jeffsol SG-522 is a sucrose- and glycerin-based polyol having a hydroxyl value of 522.

Jeffsol G31-28 refers to a glycerol based EO/PO polyol with hydroxyl value of 28.

Surfonic N-95 is a surfactant being the 9.5-mole ethoxylate of nonylphenol.

Tegostab B8870 is a foam stabilizer of the type polyether polysiloxane.

Rubinate M is a pMDI isocyanate with iso-value 31.5.

The formulation II did not result in a rigid PU-packaging foam, as the foam collapsed during rise. Formulation I resulted in a rigid PU-packaging foam, after foaming with cream time of only 7 seconds, and an end of rise at 102 seconds.

Hence the secondary amine bis-(N,N-2-dimethylamino-ethoxy-ethyl)-amine has the advantage over the methylated tertiary amine bis-(N,N-2-dimethyl-aminoethoxyethyl)methylamine that it can be used as rigid foam catalyst, where the methylated version may fail.

It is understood that the above-mentioned method may be adapted or modified by the skilled person to accommodate the needs.

It is to be understood that although preferred embodiments and/or materials have been discussed for providing embodiments according to the present invention, various modifications or changes may be made without departing from the scope and spirit of this invention.

The invention claimed is:

1. A secondary amine with formula $(R^1R^2NR^3)_2NH$, wherein
each of $R^1$ and $R^2$ are a methyl group;
$R^3$ being —$CH_2CH_2OCC_2CH_2$—.

2. A mixture comprising a secondary amine with formula $(R^1R^2NR^3)_2NH$, wherein each of $R^1$ and $R^2$ are a methyl group and $R^3$ being —$CH_2CH_2OCH_2CH_2$—,
and 0.1% w to 20% w of bis(N,N-2-dimethylaminoethoxyethyl)methylamine wherein the % w is based on the total weight of the mixture.

3. The mixture according to claim 2, wherein the secondary amine with formula $(R^1R^2NR^3)_2NH$ is present in an amount of more than 80% w and bis(N,N-2-dimethylaminoethoxyethyl)methylamine is present in an amount of 1% w to 18% w and wherein the % w is based on the total weight of the mixture.

4. A composition for providing polyurethanes comprising a secondary amine with formula $(R^1R^2NR^3)_2NH$ wherein each of $R^1$ and $R^2$ are a methyl group and $R^3$ being —$CH_2CH_2OCH_2CH_2$—;
an isocyanate; and
an isocyanate reactive compound.

* * * * *